United States Patent
Yordinsky

(10) Patent No.: US 6,837,711 B1
(45) Date of Patent: Jan. 4, 2005

(54) DENTURE ADHESIVE SHEET CUSTOM CUTTING SYSTEM

(76) Inventor: Sol Yordinsky, 23 Dongan Hills Ave., Staten Island, NY (US) 10306

( * ) Notice: Subject to any disclaimer, the term of this patent is extended or adjusted under 35 U.S.C. 154(b) by 0 days.

(21) Appl. No.: 10/151,843

(22) Filed: May 21, 2002

(51) Int. Cl.$^7$ ............................. A61C 13/12; A61K 6/00
(52) U.S. Cl. ...................... 433/168.1; 433/180; 523/120
(58) Field of Search ............................. 433/168.1, 180; 523/120; 264/16, 17

(56) References Cited

U.S. PATENT DOCUMENTS

| | | | |
|---|---|---|---|
| 4,239,488 A | 12/1980 | Sempler | 433/180 |
| 4,503,116 A * | 3/1985 | Lapidus | 428/286 |
| 4,516,938 A | 5/1985 | Hall | 433/215 |
| 5,658,586 A * | 8/1997 | Rajaiah et al. | 424/435 |
| 5,803,737 A | 9/1998 | Lyalin | 433/223 |
| 6,186,790 B1 | 2/2001 | Karmaker | 433/215 |
| 6,276,937 B1 | 8/2001 | Gasman | 433/168.1 |
| 6,294,594 B1 * | 9/2001 | Borja et al. | 523/120 |

* cited by examiner

Primary Examiner—Ralph A. Lewis
(74) Attorney, Agent, or Firm—Goldstein Law Offices, P.C.

(57) ABSTRACT

A dental prosthesis adhesive sheet trimming method, for allowing a user to custom trim an untrimmed dental adhesive sheet to create a trimmed dental adhesive sheet which is custom sized to fit the user's dental prosthesis. The dental prosthesis has a ridge recess for accommodating the dental adhesive sheet. The overall outline of the dental prosthesis is traced, which is used to create a final outline which is uniformly eroded along its edges than the overall outline. To allow the user to easily trim the untrimmed dental adhesive sheets to fit the ridge recess, a die is created from the final outline which may be employed by the user to create trimmed dental adhesive sheets wherever needed for use to affix the dental prosthesis within the mouth.

11 Claims, 6 Drawing Sheets

DENTURE ADHESIVE SHEET CUSTOM CUTTING SYSTEM

BACKGROUND OF THE INVENTION

The invention relates to a denture adhesive sheet custom cutting system. More particularly, the invention relates to a system which allows a user to easily custom cut untrimmed denture adhesive sheets.

Millions of Americans wear dentures. As natural dental structures exceed their useful life, "dentures" are fabricated to act as a prosthetic replacement. Dentures are typically held in place using a variety of adhesives. Traditional adhesives are provided in powder, gel, and paste form which adheres the upper ridge of the dentures within the mouth. However, such gels are undesirable, in that they are messy, are typically applied by the user unevenly with unpredictable results, and frequently dilute rapidly in saliva to create an uneven seal.

An improved adhesive has been provided in recent years in the form of a paper-like sheet or wafer, generally under the trademark SEA-BOND, as disclosed in U.S. Pat. No. 4,503,116 to Lapidus. The sheet is made of thermally laminated fabrics having an adhesive which is ordinarily non-sticky, but is activated by fluids within the mouth to provide adhesive qualities and to expand and fill crevices. In the case of lower dentures, the sheet is provided in a "boomerang" shape, which follows and is meant to fit within the ridge recess created at the top of the prosthesis (opposite from the prosthetic teeth). The ridge recess follows the contours of the denture, slightly within the overall outline thereof. The sheet is inserted into the ridge, and the denture is adhered to oral mucosa at the lower jaw. However, as dental anatomy will differ from patient to patient, one size does not necessarily fit all users. Accordingly, wearers/users are encouraged to trim the sheet using a pair of scissors, until the sheet fits neatly within the ridge recess of the dentures.

Generally dentures are removed for cleaning daily, and thus must be reinserted each morning. Accordingly, the operation of trimming the adhesive sheet also becomes a daily operation. Unfortunately, most denture wearers tend to be advanced in age, and thus are likely to have limited dexterity. Accordingly, the operation of trimming the adhesive sheet can be difficult, if not impossible for many denture wearers.

SUMMARY OF THE INVENTION

It is an object of the invention to produce a system which allows denture adhesive sheets to be custom fit for the user with minimal effort. Accordingly, the present invention provides employs a die to cut the adhesive sheet without requiring significant dexterity.

It is another object of the invention to provide a system which is easily customized for a particular user. Accordingly, the die is custom configured for the particular user so that the adhesive sheet cut thereby fits neatly within the ridge recess of the dentures.

It is still another object of the invention to provide a system which allows the die to be created from the existing dentures. As the dental prosthesis generally follows the contours of the ridge recess, an outline is recorded of the dental prosthesis which is used to create the die. A photo process may be employed by which the outer shadow of the denture is registered and shrunk slightly to create a sharp edge of the die which is used for cutting the dental adhesive sheets.

The invention is a dental prosthesis adhesive sheet trimming method, for allowing a user to custom trim an untrimmed dental adhesive sheet to create a trimmed dental adhesive sheet which is custom sized to fit the user's dental prosthesis. The dental prosthesis has a ridge recess for accommodating the dental adhesive sheet. The overall outline of the dental prosthesis is traced, which is used to create a final outline which is eroded consistently from the overall outline. To allow the user to easily trim the untrimmed dental adhesive sheets to fit the ridge recess, a die is created from the final outline which may be employed by the user to create trimmed dental adhesive sheets wherever needed for use to affix the dental prosthesis within the mouth.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
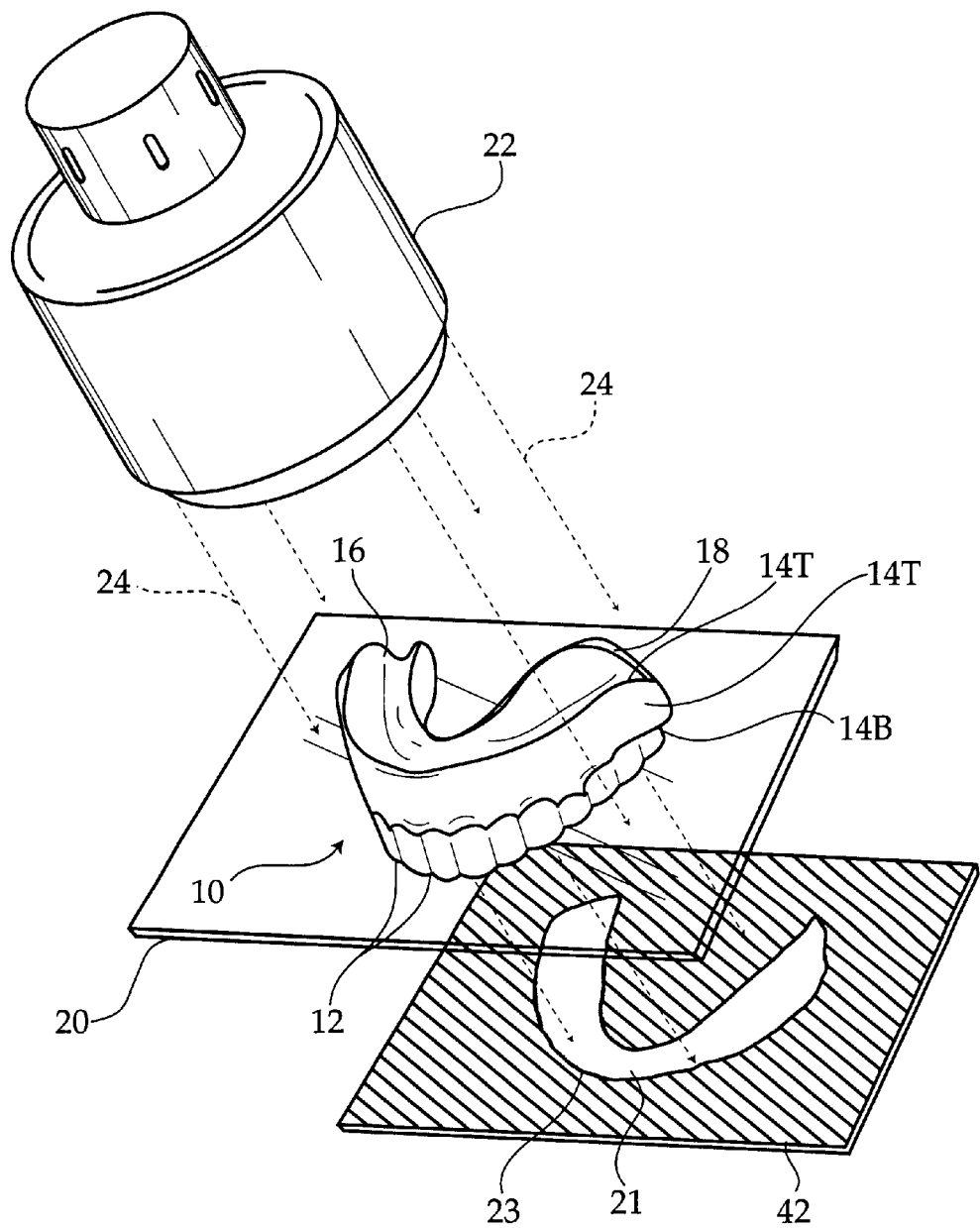
FIG. 1 is a diagrammatic perspective view, illustrating a final outline of a dental prosthesis being created through a photo process.

FIG. 1 illustrates a dental prosthesis 10, also known as a denture, which is associated with and worn by a user. The dental prosthesis 10 a common structure 14 having a bottom 14B and a top 14T. The common structure 14 is configured to resemble the human gums. Prosthetic teeth 12 are located at the bottom 14B, and a ridge recess 16 extends on the common structure 14, and is defined by a lip 18. The lip 18 substantially follows a top plan of the common structure 14 or overall outline at the top 14T of the dental prosthesis 10. The ridge recess 16 is a valley created by the lip 18.

In FIG. 1 a photo process is being used to create a shadow image 21 on a first photosensitive film 42. It should be noted that the first photo sensitive film 42 may be any material or device capable of registering a photo image in a useable form. Accordingly, the first photo sensitive film 42 may be photo sensitive paper, film, or any other suitable current or prospective technology capable of registering or recording an image.

According to the photo process, the dental prosthesis 10 is resting upon a transparent bed 20, with the prosthetic teeth 12 resting upon the bed 20. A light source 22 is positioned above the bed 20, directly over the dental prosthesis 10, such that it produces incident light 24 which will partially travel through the bed 20 and become transmitted light 26, and will be partially blocked by the dental prosthesis 10. Accordingly a shadow image 21, having a shadow image outline 23 having edges equivalent in size to an overall outline of the dental prosthesis (in plan view) is created below the bed 20. This image may be formed and manipulated in a variety of ways. However, according to the present invention, the first photosensitive film 42 is positioned below the bed 20 to register the shadow image 21.

Figure 1A:
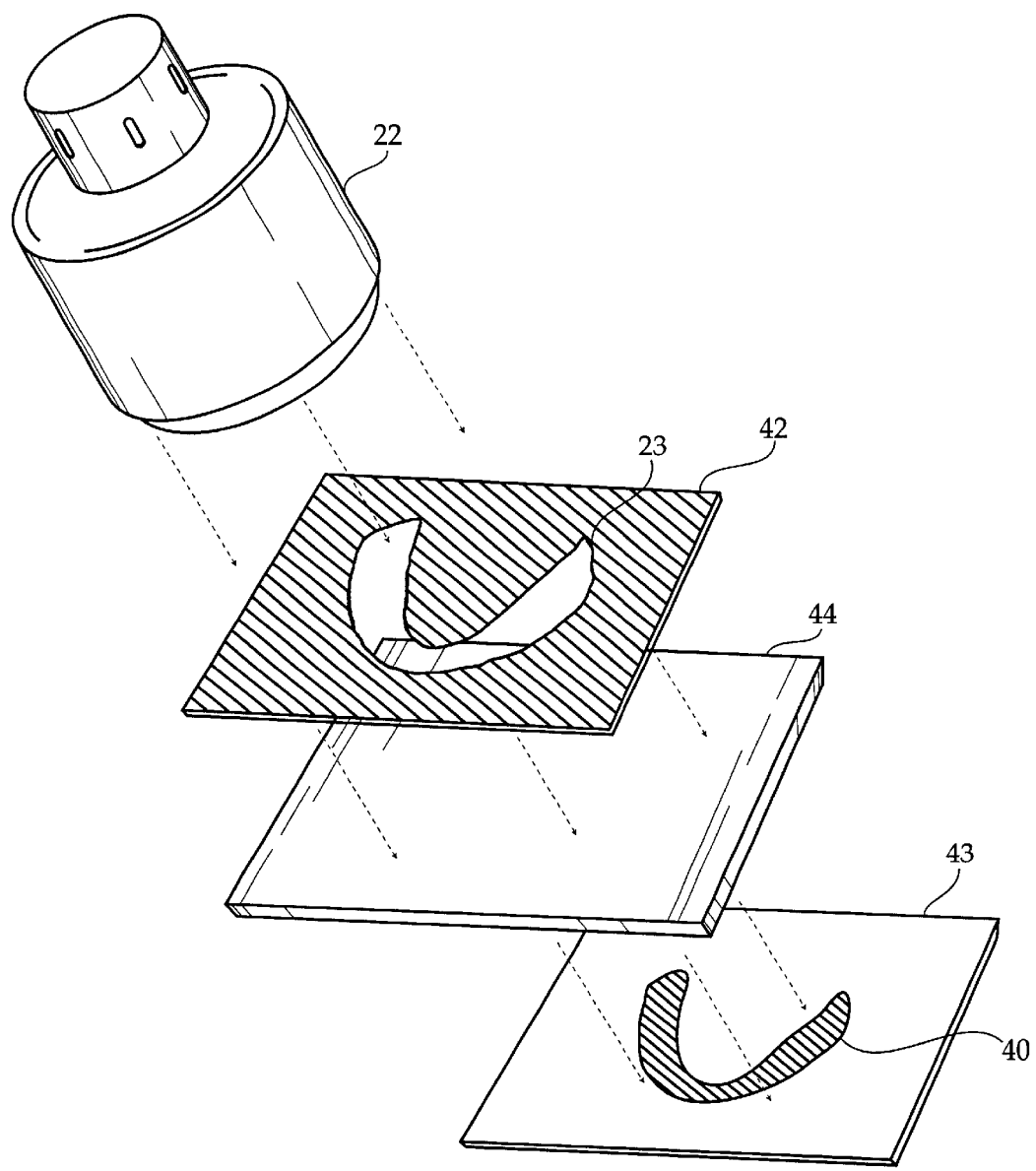

Once the shadow image 21 has been formed, it is necessary to "shrink" the shadow image outline 23, so that all edges are eroded. In other words, a simple reduction would cause edges within the "boomerang" to come closer together. What is desired is that all edges are eroded inward, preferably by 1/16" of an inch, to reflect the actual size of the ridge recess 16 which is naturally that size. Referring to FIG. 1A, a subsequent photo process may be employed, by which a second photosensitive film 43 is provided. A diffusion sheet 44 is placed between the first photosensitive film 42 and second photosensitive film 43. The light source 22 is positioned above the first photosensitive film 42 so that light is directed upon the first photosensitive film 42, through the diffusion sheet 44, and onto the second photosensitive film 42. As seen in FIG. 1A, a final outline 40 is formed on the second photosensitive film 42.

Figure 1B:
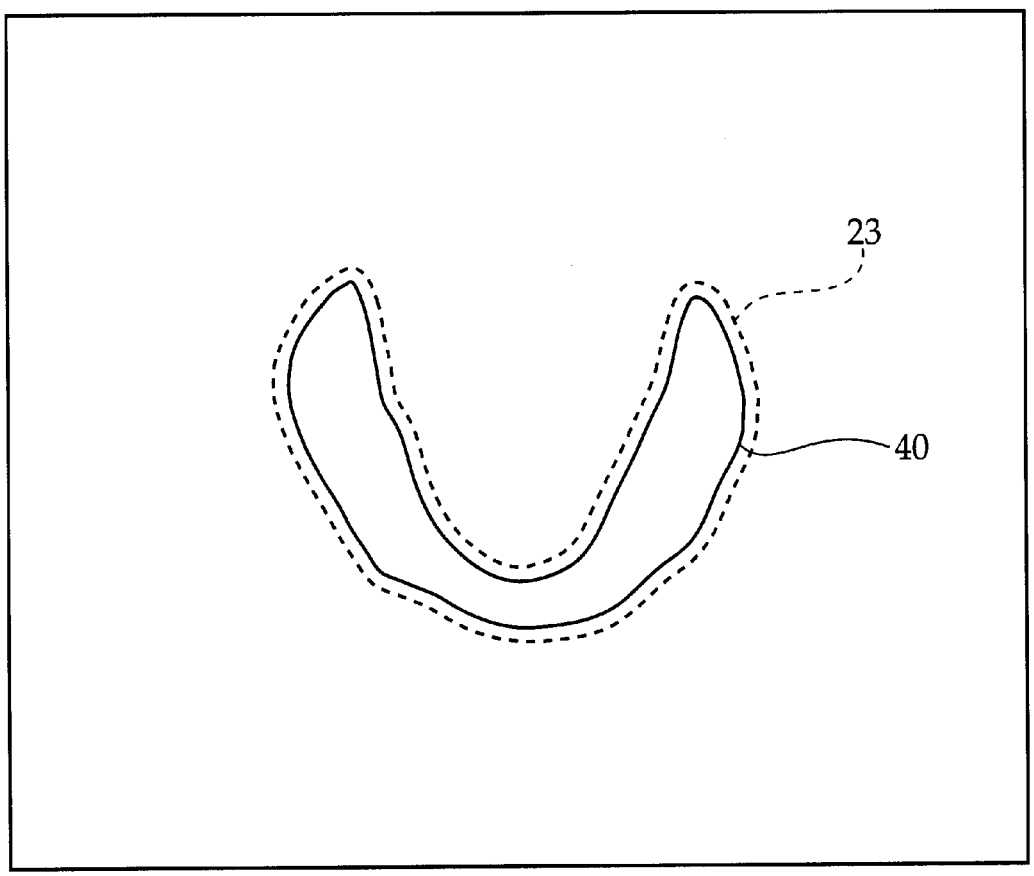

Referring to FIG. 1B which offers a comparison between the final outline 40 and the shadow image outline 23, the final outline 40 is a photographic shrink of the final outline 40, whereas the shadow image outline 23 has been eroded uniformly to create the final outline 40. As previously stated, for the intended purposes it is preferred that the final image outline 40 is consistently 1/16" smaller than the shadow image outline 23, which should make it consistently 1/16" smaller than the overall outline of the dental prosthesis.

Illustrated in FIG. 1, FIG. 1A, and FIG. 1B is a system for creating the photographic shrink. However, if the first photosensitive film 42 is conventional photographic transparency film, the image created in FIG. 1 might actually be reversed—with a back shadow image 21 created on a clear background, and a negative would then need to be created before proceeding to the step illustrated in FIG. 1A. However, to the extent that negative and positives would need to be created in between the steps illustrated, one of ordinary skill in the art would make adjustments in the processing as appropriate to the particular materials used. Such specific manipulation is unimportant to the present invention, since it should be well appreciated by those skilled in the art that other systems can be employed, either mechanical, chemical, or electronic to create both the shadow image and the final outline. For example, the shadow image might be registered on a conventional digital image scanner and the final outline can be easily created from its shadow image outline using computer software requiring only minimum complexity.

Figure 2:
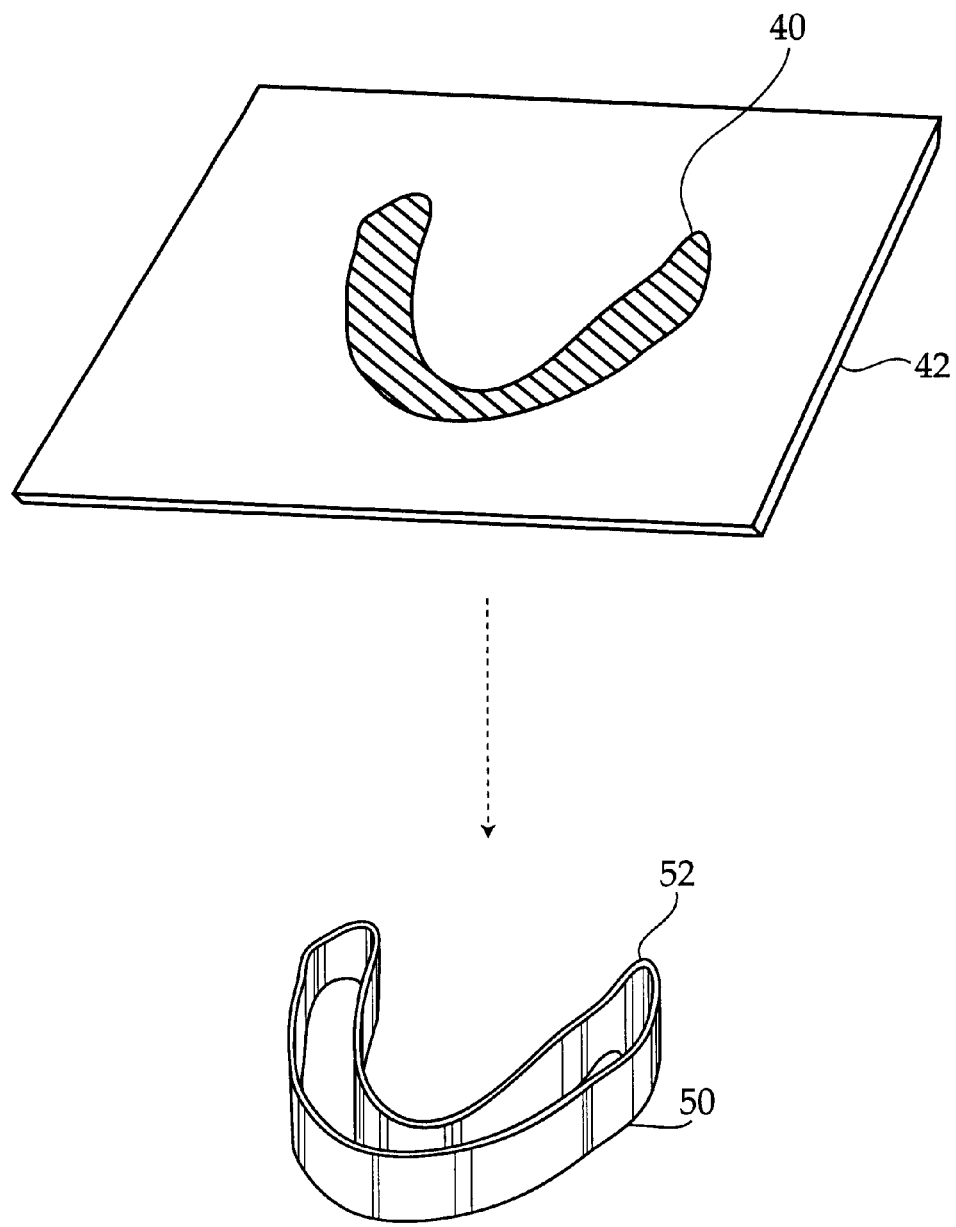
FIG. 2 illustrates that a die is created which has a sharp edge sized and shaped like the final outline created by the photo process of FIG. 1.

As illustrated in FIG. 2, a die 50 is created from the final outline 40 on the second photosensitive film 43. The die may be fabricated by a variety of manufacturing processes. For example it may be extruded from an opening shaped like the final outline 40. The die 50 has a sharp edge 52, which is shaped like the final outline 40. The die may further be fabricated using other techniques by which the overall outline is traced, to create a final outline which represents the slightly smaller ridge recess. As used herein "sharp" edge does not necessarily mean sharpened to a point or beveled, however it is a edge which is capable of making an impression and a cut, and "stamping a cut-out" as in conventional die-cut manufacturing.

Figure 3:
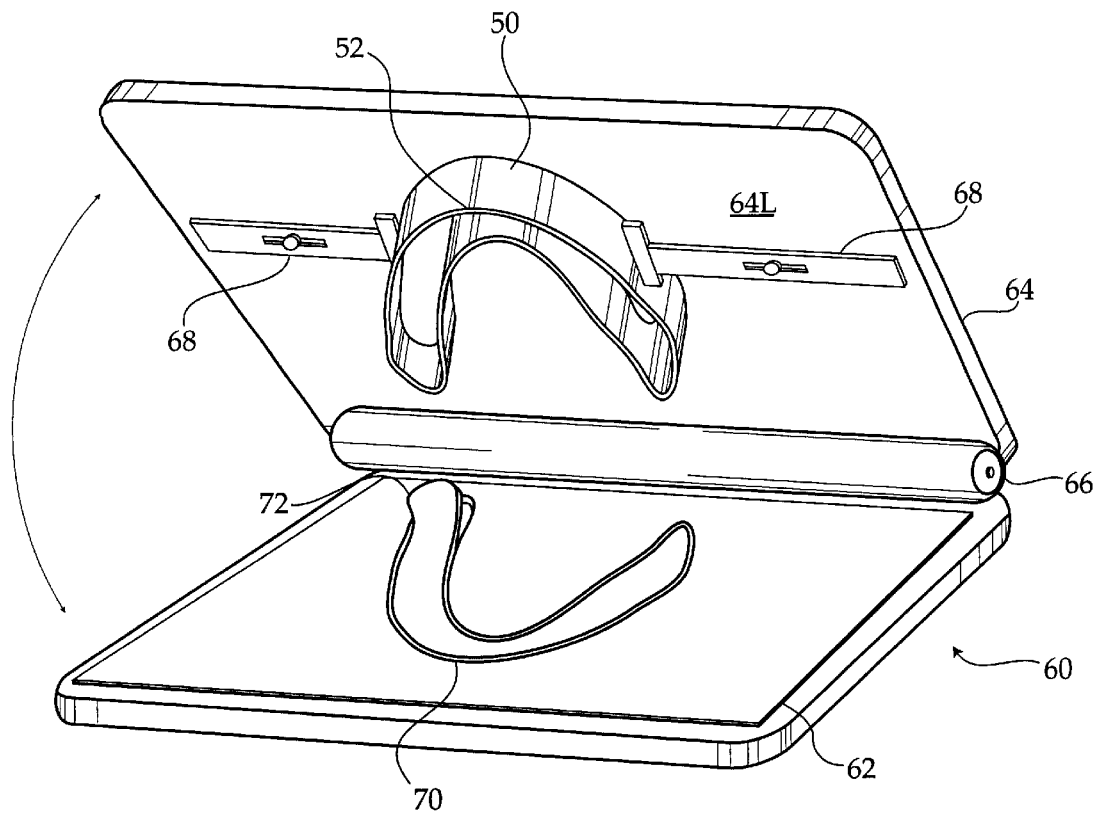
FIG. 3 illustrates that the die has been inserted into a portable die cutting machine, which has been subsequently used to make a custom cut-out in the adhesive sheet.

Referring now to FIG. 3, a die cutting machine 60 is provided, having a base 62 and an actuating arm 64. The actuating arm is attached to the base 62 with a hinge 66 so that it is movable toward and away from the base 62. The actuating arm 64 has a lower surface 64L which has a die holder 68 which is adjustable to secure dies of different sizes. Illustrated in FIG. 3, the die 50 fabricated in FIG. 2 for the user is held tightly on the lower surface 64L with the die holder 69, with the sharp edge 52 oriented toward the base.

Also illustrated in FIG. 3, an untrimmed dental adhesive sheet 70, having a boomerang shape, is positioned upon the base 62 so that it is properly aligned with the die 50. Indicia, a clip, or other means may be provided to show a user where to properly position the dental adhesive sheet 70 on the base 62. In particular, the dental adhesive sheet 70 must be positioned so that when the actuating arm 64 is brought down toward the base, the entire sharp edge 52 of the die 50 engages the adhesive sheet 70.

Thus, to effect the trimming of the adhesive sheet 70 to customize the sheet to fit the dentures belonging to the user, the user presses the actuating arm 64 downward to move the actuating arm 64 toward the base and thus move the die 50 toward the base, such that the sharp edge 52 of the die 50 engages the untrimmed dental adhesive sheet 70 positioned upon the base 62. With sufficient pressure upon the actuating arm 64 and thus the die 50, a custom trimmed adhesive sheet 72 is created, and may be removed from the remainder of the untrimmed adhesive sheet 70, as seen in FIG. 3.

Figure 4:
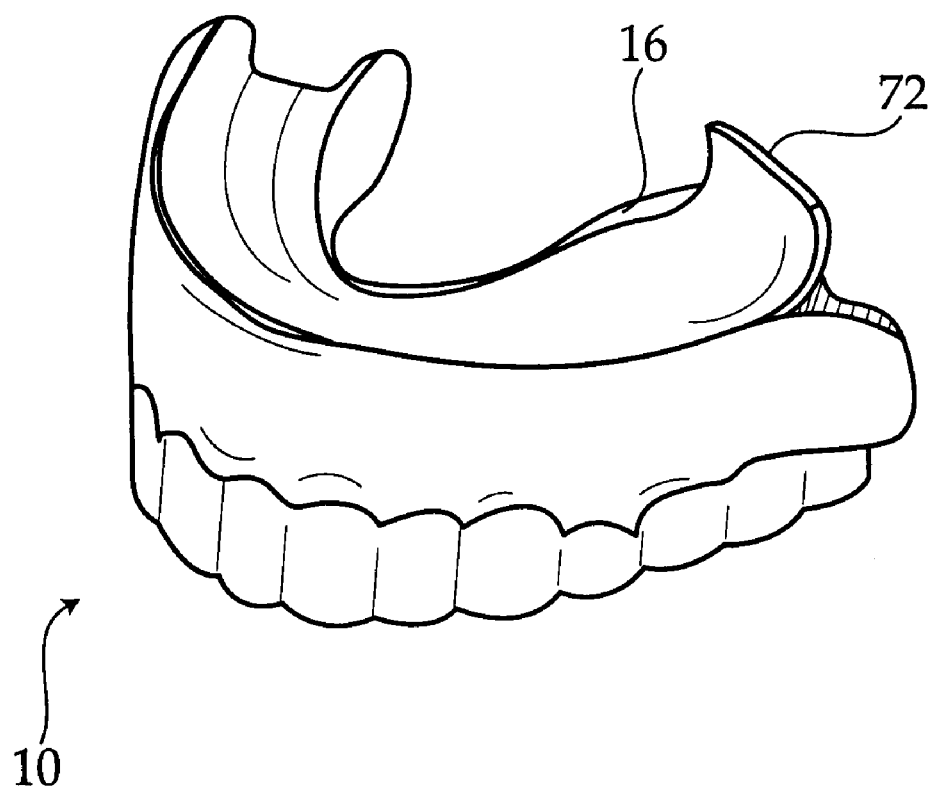
FIG. 4 illustrates that the custom cut adhesive sheet fits neatly within the ridge in the dental prosthesis.

Referring now to FIG. 4, the custom trimmed adhesive sheet 70 is fitted within the ridge recess 16 by the user. By virtue of the shrink performed optically in FIG. 1, the custom trimmed adhesive sheet 72 fits neatly within the ridge recess. As previously stated, in general, custom trimmed adhesive sheet 72 need be approximately one sixteenth of an inch (1/16") smaller than the overall outline of the denture to properly fit within the ridge recess. Now, once the custom trimmed adhesive sheet 72 is seated neatly within the ridge recess 16, the denture 10 can be inserted into the user's mouth, positioned therein, and mated with oral mucosa therein so that it is affixed in place.

As used herein "user" can mean both the person wearing the dentures, as well as a caregiver having the dexterity to manipulate the die, untrimmed dental adhesive sheet, and any associated machinery so as to perform the trimming operation. As denture wearers tend to be advanced in age as previously noted, it is often not the wearers themselves, but people closely associated with them, or even a dental lab, who might perform the trimming operation from the custom made die.

It should be noted that the denture prosthesis illustrated in the drawing figures is for use on the lower jaw of the user. However, the inventive system can be similarly employed for use in trimming adhesive sheets for dental prosthesis intended for the upper jaw as well. As upper jaw dental prosthesis generally has a central film which is adhered within the mouth to the maxilla, adhesive sheets used with upper jaw dental prosthesis are generally circular in shape, with a notch cut-out. These adhesive sheets are typically adhered against the central film. Accordingly, the step of creating the die from the final outline might be modified somewhat. However, such modification could be readily made by one of ordinary skill in the art, following the inventive method disclosed herein.

In conclusion, herein is presented a system for allowing dental adhesive sheets to be custom cut by a user with minimum effort, by creating a die which is custom shaped according to the dental prosthesis worn by the user, so that trimmed dental adhesive sheets can be stamped-out of an untrimmed dental adhesive sheet by the user when needed.

The system is shown by example in the accompanying drawing figures. In this regard, numerous variations are possible while adhering to the inventive system. Such variations are contemplated as being a part of the present invention.

What is claimed is:

1. A method for trimming denture adhesive sheets by a user, the user having a dental prostheses having a bottom having prosthetic teeth and a top having a ridge recess defined by a lip, comprising the steps of:

creating a die having a sharp edge sized and shaped like the ridge recess of the dental prostheses of the user;

creating a trimmed denture adhesive sheet from an untrimmed denture adhesive sheet by the user with the die;

inserting an trimmed denture adhesive sheet into the ridge recess of the dental prosthesis; and inserting the dental prosthesis into the user's mouth.

2. The method for trimming denture adhesive sheets as recited in claim 1, wherein the step of creating a die further comprises the step of:

tracing the overall outline of the dental prosthesis;

creating a final outline by uniformly eroding the traced overall outline of the dental prosthesis;

fabricating the die to follow the eroded traced final outline.

3. The method for trimming denture adhesive sheets as recited in claim 2, wherein the step of tracing the overall outline of the dental prosthesis further comprises:

placing the dental prosthesis on a bed;

shining a light source from above the bed upon the dental prosthesis; and casting a shadow image having a shadow image outline beneath the bed by the dental prosthesis.

4. The method for trimming denture adhesive sheets as recited in claim 3, wherein the step of creating the die further comprises creating a shadow image outline on a photosensitive film.

5. The method for trimming denture adhesive sheets as recited in claim 4, wherein the step of creating the die further comprises shrinking the shadow image outline uniformly along its edges to create the final outline.

6. The method for trimming denture adhesive sheets as recited in claim 5, wherein the step of creating the die further comprises shrinking the shadow image outline by substantially $\frac{1}{16}$ of an inch uniformly along its edges.

7. The method for trimming denture adhesive sheets as recited in claim 1, further comprising the steps of:

providing a die cutting machine having a base and an actuating arm;

attaching the die to the actuating arm with the sharpened edge of the die oriented toward the base; and wherein the step of trimming the untrimmed denture adhesive sheet further comprises:

positioning the die on the actuating arm;

positioning the untrimmed denture adhesive sheet onto the base; and creating the trimmed denture adhesive sheet by pressing the die downward against the untrimmed denture adhesive sheet by pressing the actuating arm downward toward the base.

8. The method for trimming denture adhesive sheets as recited in claim 7, wherein the step of creating a die further comprises the step of:

tracing the overall outline of the dental prosthesis;

creating a final outline by uniformly eroding the traced overall outline of the dental prosthesis;

fabricating the die to follow the eroded traced final outline.

9. The method for trimming denture adhesive sheets as recited in claim 8, wherein the step of tracing the overall outline of the dental prosthesis further comprises:

placing the dental prosthesis on a bed;

shining a light source from above the bed upon the dental prosthesis; and casting a shadow image having a shadow image outline beneath the bed by the dental prosthesis.

10. The method for trimming denture adhesive sheets as recited in claim 9, wherein the step of creating the die further comprises creating a shadow image outline on a photosensitive film.

11. The method for trimming denture adhesive sheets as recited in claim 10, wherein the step of creating the die further comprises shrinking the shadow image outline uniformly along its edges to create the final outline.

* * * * *